US012806194B2

(12) United States Patent
Choi et al.

(10) Patent No.: US 12,806,194 B2
(45) Date of Patent: Nov. 24, 2026

(54) PHARMACEUTICAL COMPOSITION FOR CANCER PREVENTION OR TREATMENT, COMPRISING CDK4/6 INHIBITOR AND TRICYCLIC ANTIDEPRESSANT

(71) Applicant: NATIONAL CANCER CENTER, Goyang-si (KR)

(72) Inventors: Yong Doo Choi, Goyang-si (KR); Sung Ho Goh, Goyang-si (KR)

(73) Assignee: NATIONAL CANCER CENTER, Goyang-si (KR)

( * ) Notice: Subject to any disclaimer, the term of this patent is extended or adjusted under 35 U.S.C. 154(b) by 435 days.

(21) Appl. No.: 18/576,427

(22) PCT Filed: Jun. 30, 2022

(86) PCT No.: PCT/KR2022/009462

§ 371 (c)(1),
(2) Date: Jan. 4, 2024

(87) PCT Pub. No.: WO2023/282544

PCT Pub. Date: Jan. 12, 2023

(65) Prior Publication Data

US 2024/0307393 A1 Sep. 19, 2024

(30) Foreign Application Priority Data

Jul. 6, 2021 (KR) ........................ 10-2021-0088445

(51) Int. Cl.

| | |
|---|---|
| ***A61K 31/506*** | (2006.01) |
| ***A61K 31/135*** | (2006.01) |
| ***A61K 31/519*** | (2006.01) |
| ***A61K 31/55*** | (2006.01) |
| ***A61P 35/00*** | (2006.01) |

(52) U.S. Cl.

CPC .......... *A61K 31/506* (2013.01); *A61K 31/135* (2013.01); *A61K 31/519* (2013.01); *A61K 31/55* (2013.01); *A61P 35/00* (2018.01)

(58) Field of Classification Search

CPC ................ A61K 31/506; A61K 31/135; A61K 31/519; A61K 31/55; A61P 35/00

USPC .......................................................... 514/217

See application file for complete search history.

(56) References Cited

U.S. PATENT DOCUMENTS

| | | | |
|---|---|---|---|
| 2014/0107114 A1 | 4/2014 | Kim et al. | |
| 2014/0271727 A1 | 9/2014 | Hwang et al. | |
| 2019/0160148 A1 | 5/2019 | Beckmann et al. | |

FOREIGN PATENT DOCUMENTS

| | | |
|---|---|---|
| ES | 2 363 394 A1 | 8/2011 |
| JP | 2018-8914 A | 1/2018 |
| WO | WO 2014/018563 A2 | 1/2014 |

OTHER PUBLICATIONS

Cancer [online], [retrieved on Jul. 6, 2007] Retrieved from the Internet, URL: http://www.nim.nih.gov/medlineplus/cancer.html (Year: 2007).*

Lala et al., Role of nitric oxide in tumor progression: Lessons from experimental tumors, Cancer and Metastasis Reviews (1998), 17 91-106 (Year: 1998).*

Golub et al., Molecular Classification of Cancer: Class Discovery and Class Prediction by Gene Expression Monitoring, Science (1999), vol. 286, 531-537 (Year: 1999).*

International Search Report mailed on Oct. 5, 2022 in PCT/KR2022/009462 filed on Jun. 30, 2022 (2 pages).

Alburquerque-Gonzalez, B. et al. "New role of the antidepressant imipramine as a Fascinl inhibitor in colorectal cancer cells", Experimental & Molecular Medicine, 2020, vol. 52, pp. 281-292.

Bellet, M. et al. "Palbociclib and ribociclib in breast cancer: consensus workshop on the management of concomitant medication", Therapeutic Advances in Medical Oncology, 2019, vol. 11, pp. 1-43.

Zingone, A. et al. "Relationship between anti-depressant use and lung cancer survival", Cancer Treatment and Research Communications, 2017, vol. 10, pp. 33-39.

Japanese Office Action issued May 7, 2025 in Japanese Application No. 2024-500343, 3 pages.

Extended European Search Report Issued May 28, 2025 in European Patent Application No. 22837896.4, 11 pages.

Poratti et al., "Third-generation CDK inhibitors: A review on the synthesis and binding modes of Palbociclib, Ribociclib and Abemaciclib", European Journal of Medicinal Chemistry, vol. 172, 2019, pp. 143-153.

Liu et al., "Mechanisms of the CDK4/6 inhibitor palbociclib (PD 0332991) and its future application in cancer treatment (Review)", Oncology Reports, vol. 39, 2018, pp. 901-911.

Arimochi et al., "Characterization of cytotoxic actions of tricyclic antidepressants on human HT29 colon carcinoma cells", European Journal of Pharmacology, vol. 541, 2006, pp. 17-23.

Pilkington et al., "The role of tricyclic drugs in selective triggering of mitochondrially-mediated apoptosis in neoplastic glia: a therapeutic option in malignant glioma?", Radiology Oncology, vol. 40, No. 2, 2006, pp. 73-85.

(Continued)

*Primary Examiner* — Kristin A Vajda

(74) *Attorney, Agent, or Firm* — Oblon, McClelland, Maier & Neustadt, L.L.P.

(57) ABSTRACT

It is an object of the present invention to provide a composition for ameliorating, preventing or treating cancer, comprising a CDK4/6 inhibitor and a tricyclic antidepressant as active ingredients. If the composition comprising a CDK4/6 inhibitor and a tricyclic antidepressant according to the prevention invention is administered in combination, anticancer synergistic effects are exhibited such that the survival rate of cancer cells is remarkably reduced compared to that of a group treated with the CDK4/6 inhibitor or tricyclic antidepressant alone. In addition, since the effect of reducing side effects of CDK4/6 inhibitors is also exhibited by administration of the composition according to the present invention, the composition comprising a CDK4/6 inhibitor and a tricyclic antidepressant as active ingredients can be effectively used as a preventive or therapeutic agent for cancer.

8 Claims, 6 Drawing Sheets

(56) References Cited

OTHER PUBLICATIONS

Yuan et al., "Nortriptyline induces mitochondria and death receptor-mediated apoptosis in bladder cancer cells and inhibits bladder tumor growth in vivo", European Journal of Pharmacology, vol. 761, 2015, pp. 309-320.

* cited by examiner

Figure 3b

| | Control (n=7) | Desipramine (n=7) | Abemaciclib (n=7) | Combination (n=7) |
|---|---|---|---|---|
| ALT (U/L) | 32.29±8.20 | 29.00±4.24 | 33.43±3.99 | 30.71±5.28 |
| AST (U/L) | 150.71±66.98 | 106.71±23.98 | 95.00±16.97 | 89.14±37.79 |
| ALP (U/L) | 100.00±10.25 | 79.43±9.27 | 114.00±14.40 | 99.14±13.13 |
| Glu (mg/dL) | 275.86±52.16 | 220.43±63.12 | 176.43±33.16 | 211.14±51.57 |
| BUN (mg/dL) | 19.51±2.86 | 21.50±2.90 | 24.99±1.81 | 24.03±3.25 |
| Crea (mg/dL) | 0.10±0.00 | 0.13±0.05 | 0.10±0.00 | 0.10±0.00 |
| T-Bili (mg/dL) | 0.16±0.05 | 0.14±0.05 | 0.16±0.05 | 0.19±0.07 |
| T-chol (mg/dL) | 89.57±1.90 | 85.57±5.16 | 82.00±16.82 | 111.43±15.76 |
| TG (mg/dL) | 109.00±22.51 | 82.57±31.76 | 153.71±33.69 | 160.43±31.46 |
| TP (g/dL) | 4.33±0.29 | 4.56±0.36 | 4.19±0.24 | 4.39±0.31 |
| Alb (g/dL) | 2.66±0.10 | 2.57±0.05 | 2.60±0.13 | 2.61±0.16 |

PHARMACEUTICAL COMPOSITION FOR CANCER PREVENTION OR TREATMENT, COMPRISING CDK4/6 INHIBITOR AND TRICYCLIC ANTIDEPRESSANT

CROSS REFERENCE TO RELATED APPLICATIONS

This application is a National Stage entry under 35 U.S.C. § 371 of PCT/KR2022/009462, filed on Jun. 30, 2022, and claims priority to KR Patent Application No. 10-2021-0088445, filed on Jul. 6, 2021, the entire contents of which are incorporated herein by reference.

TECHNICAL FIELD

The present invention relates to a pharmaceutical composition for ameliorating, preventing or treating cancer, comprising a CDK4/6 inhibitor and a tricyclic antidepressant as active ingredients.

BACKGROUND ART

Cyclin-dependent kinase (CDK) is an enzyme that regulates cell division and proliferation, and cell cycle progression is controlled by cyclins and their associated CDKs. Most cancer cells exhibit dysregulated CDKs, and CDK inhibition is emerging as a potential treatment for various cancers. CDK4/6 is responsible for regulating the progression from G1 phase of the cell cycle to S phase by phosphorylating cyclin protein D1 to increase its activity.

A CDK4/6 inhibitor is a drug that blocks the formation of the CDK4/6-cyclin D1 complex and stops cell division, and three inhibitors, palbociclib, ribociclib and abemaciclib, were approved for the treatment of HR(+), HER2(−) advanced or metastatic breast cancer (U.S. Pharm. 2020; 45(5) (Specialty&Oncology suppl):3-8). In addition, clinical trials have been conducted using the CDK4/6 inhibitor as a combination therapy with letrozole or fulvestrant, which are drugs used to treat breast cancer.

However, it was reported that various side effects occur with the use of CDK4/6 inhibitors, most side effects are low-risk side effects of level 1 or 2, and side effects such as level 3-4 gastrointestinal disorders, neutropenia and leukopenia also occur frequently. If side effects occur, measures are taken to reduce side effects by discontinuing the use of the CDK4/6 inhibitor or reducing the amount used.

On the one hand, in the case of cancer patients, the incidence of depression is high due to the pain experienced during the treatment process, so that antidepressants are frequently prescribed to solve this problem, and the prescriptions are carried out in various concentration ranges. It is known that the side effects due to antidepressant prescriptions include insomnia, weight loss, dry mouth, chest pain, and the like, but unlike the side effects of CDK4/6 inhibitors, there are no dangerous side effects such as decreased blood cells (Oncology (Williston Park). 33(2):62-8.)

In addition, a study investigating the survival rate of cancer patients according to the use of antidepressants showed the results that the survival rate of cancer patients did not worsen due to the use of antidepressants, and in particular, in the case of tricyclic antidepressants, the survival rate significantly increased in the lung cancer patient group (Cancer Treat Res Commun. 2017; 10: 33-39.)

Under these backgrounds, as a result of intensive research efforts to develop a method that may maximize the anti-cancer effect while minimizing side effects, the present inventors have confirmed that excellent anti-cancer effects are exhibited when the CDK4/6 inhibitor and the tricyclic antidepressant are administered in combination, and have completed the present invention.

DISCLOSURE

Technical Problem

It is an object of the present invention to provide a pharmaceutical composition for preventing or treating cancer, comprising a CDK4/6 inhibitor and a tricyclic antidepressant as active ingredients.

The technical problems to be achieved according to the technical idea of the invention disclosed in the present specification are not limited to the above-mentioned problems to be solved, and other problems not mentioned will be clearly understood by those skilled in the art from the description below.

Technical Solution

These will be described in detail as follows. On the other hand, each description and embodiment disclosed in the present application may also be applied to each other description and embodiment. That is, all combinations of the various elements disclosed in this application fall within the scope of this application. In addition, it cannot be seen that the scope of the present application is limited by the specific descriptions described below.

In an aspect for achieving the above objects, the present invention provides a pharmaceutical composition for preventing or treating cancer, comprising a CDK4/6 inhibitor and a tricyclic antidepressant as active ingredients.

The term "CDK (Cyclin-dependent kinase)" as used herein refers to a cyclin-dependent protein kinase that has the function of regulating the cell cycle, and binding to cyclin is essential for its activity. Among the CDK family, CDK 4 and CDK 6 are responsible for regulating the progression from G1 phase of the cell cycle to S phase by phosphorylating cyclin protein D1 to increase its activity.

The term "CDK4/6 inhibitor" as used herein refers to a drug that inhibits both CDK 4 and CDK 6, and CDK4/6 will be used throughout this document to refer to both CDK4 and CDK6. CDK4/6 inhibitors may be used without limitation as long as they are drugs that block the formation of the CDK4/6-cyclin D complex and stop cell division, and specifically, they may be abemaciclib, ribociclib, palbociclib, or a pharmaceutically acceptable salt thereof.

The term "tricyclic antidepressant" as used herein refers to a drug that is one of the antidepressants that has been used for a long time as a therapeutic agent for psychosis and has three rings in its chemical structure. It interferes with the reabsorption of amine-based neurotransmitters secreted from nerve endings, thereby allowing many substances to remain in the nerve junction. Specifically, the tricyclic antidepressant may be, but is not limited to, 7-OH-amoxapine, amezepine, amineptine, amitriptyline, amitriptylinoxide, amoxapine, aptazapine, azepindole, azipramine, batelapine, butriptyline, cianopramine, ciclazindol, ciclopramine, cidoxepin, clomipramine, cotriptyline, cyanodothiepin, demexiptiline, depramine (balipramine), desipramine (desmethylimipramine), desmethylclomipramine, desmethyltrimipramine, dibenzepin, dimetacrine, dosulepin (dothiepin), doxepin, enprazepine, esmirtazapine, fantridone, fluotracen, hepzidine, homopipramol, imipramine, imipraminoxide, intriptyline, iprindole, ketipramine, litracen, lofepramine, losindole, loxapine, maprotiline, mariptiline, mazindol, melitracen, metapramine, mezepine, mianserin, mirtazapine, monometarine, naranol, nitroxazepine, norbutriptyline, nordoxepin, northiaden (nordosulepin), nortriptyline (noramitriptyline), noxiptiline, octriptyline, opipramol, oxaprotiline, pipofezine, pirandamine, promethazine, propizepine, protriptyline, quinupramine, setiptiline (teciptiline), spiroxepin, tandamine, tampramine, tianeptine, tienopramine, trimipramine, imipramine blue, or a pharmaceutically acceptable salt thereof. More specifically, the tricyclic antidepressant may be amitriptyline, clomipramine, desipramine, imipramine, promethazine, or imipramine blue.

The term "active ingredient" as used herein refers to an ingredient that can exhibit the desired activity alone or exhibit activity in combination with a carrier having no activity itself.

The term "cancer (or tumor)" as used herein includes both primary and metastatic cancers without distinction. In the present invention, the cancer may be solid cancer or hematologic malignancy. Specifically, the cancer may be, but is not limited to, lung cancer, pancreatic cancer, pharynx cancer, laryngeal cancer, esophageal cancer, gastric cancer, duodenal cancer, small intestine cancer, colorectal cancer, colon cancer, rectal cancer, breast cancer, ovarian cancer, prostate cancer, liver cancer, thyroid cancer, kidney cancer, uterine cancer, brain tumor, skin cancer, melanoma, malignant bone tumor, bladder cancer, or hematologic malignancy. More specifically, the cancer may be lung cancer, colorectal cancer, or breast cancer.

The term "prevention" as used herein refers to all actions that suppress or delay the occurrence of cancer by administering the pharmaceutical composition of the present invention to an individual.

The term "treatment" as used herein refers to all actions that result in beneficial effects such as improving, relieving or ameliorating cancer by administering the pharmaceutical composition of the present invention to an individual.

The pharmaceutical composition of the present invention may be used for combined administration of the CDK4/6 inhibitor and the tricyclic antidepressant. Specifically, the pharmaceutical composition may be in the form of a mixture in which the CDK4/6 inhibitor and the tricyclic antidepressant are mixed, or the CDK4/6 inhibitor and the tricyclic antidepressant may be separately formulated and administered simultaneously or sequentially, but is not limited thereto.

When the CDK4/6 inhibitor and the tricyclic antidepressant are administered in combination, the administered concentration ratio of the CDK4/6 inhibitor and the tricyclic antidepressant may be, but is not limited to, 1:0.001 to 1:1000, specifically 1:0.003 to 1:500, 1:0.01 to 1:500, 1:0.1 to 1:500, or 1:0.7 to 1:500, more specifically 1:0.003, 1:0.01, 1:0.02, 1:0.03, 1:0.05, 1:0.08, 1:0.1, 1:1, 1:2, 1:3, 1:4, 1:5, 1:7, 1:8, 1:10, 1:11, 1:12, 1:20, 1:25, 1:100, 1:125, 1:200, or 1:500.

The pharmaceutical composition of the present invention may further comprise a pharmaceutically acceptable carrier, excipient or diluent according to conventional methods. The pharmaceutically acceptable carrier is well known in the art depending on the route of administration or formulation, and specifically, may be referred to each country's pharmacopoeia, including the 'Korean Pharmacopoeia.' The carrier, excipient and diluent that may be included in the pharmaceutical composition of the present invention may include, but are not limited to, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil. In addition, the carrier, excipient and diluent that may be included in the composition of the present invention may be, but are not limited to, unnatural carriers.

The pharmaceutical composition of the present invention may be formulated and used in the form of oral formulations such as powders, granules, tablets, capsules, suspensions, emulsions, syrups and aerosols, external preparations, suppositories or sterile injectable solutions according to conventional methods. In detail, it may be prepared using diluents or excipients, such as fillers, extenders, binders, wetting agents, disintegrants and surfactants, which are commonly used when formulated. Solid formulations for oral administration include tablets, pills, powders, granules, capsules, and the like, and such solid formulations may be prepared by mixing the compounds with one or more excipients, such as starch, calcium carbonate, sucrose, lactose and gelatin. In addition to simple excipients, lubricants such as magnesium stearate and talc may also be used. Liquid formulations for oral administration include suspensions, solutions for internal use, emulsions, syrups, and the like, and may include various excipients, such as wetting agents, sweeteners, flavoring agents and preservatives, in addition to commonly used simple diluents such as water and liquid paraffin. Formulations for parenteral administration include sterile aqueous solutions, non-aqueous solutions, suspensions, emulsions, lyophilized formulations, and suppositories. As the non-aqueous solutions and suspensions, propylene glycol, polyethylene glycol, vegetable oils such as olive oil, injectable esters such as ethyl oleate, and so on may be used. As a base of the suppositories, Witepsol, Macrogol, Tween 61, cacao butter, laurin, glycerogelatin, and so on may be used. The specific formulation of the pharmaceutical composition is known in the art, and may be referred to, for example, Remington's Pharmaceutical Sciences (19th ed., 1995), and the like. This document is considered as part of the present specification.

The pharmaceutical composition of the present invention may be applied in any formulation comprising the CDK4/6 inhibitor and the tricyclic antidepressant as active ingredients, and may be prepared as an oral or parenteral formulation. Specifically, the mode of administration includes, but is not limited to, forms suitable for oral, rectal, nasal, topical (including buccal and sublingual), subcutaneous, vaginal or parenteral (including intramuscular, subcutaneous and intravenous) administration, or forms suitable for administration by inhalation or insufflation.

The pharmaceutical composition of the present invention is administered in a pharmaceutically effective amount. The pharmaceutically effective amount refers to an amount that is sufficient to treat a disease at a reasonable benefit/risk ratio applicable to medical treatment and does not cause side effects, and the level of the effective dose may be determined depending on factors including the patient's health status, the type and severity of the disease, the activity of the drug, the sensitivity to the drug, the mode of administration, the time of administration, the route of administration and the rate of the excretion, the duration of treatment, combination and the drugs used simultaneously, and other factors well known in the medical field. The dosage and frequency of administration do not limit the scope of the present invention in any way.

The pharmaceutical composition of the present invention may be administered to mammal animals such as mice, dogs, cats, cows, horses, pigs and humans through various routes.

The administration of the present invention may be administered once a day, or may be administered in several divided doses.

The pharmaceutical composition of the present invention may be used alone or in combination with various anti-cancer therapies commonly used in the art, such as surgery, radiotherapy, hormone therapy, chemotherapy and biological response regulators. In this sense, the pharmaceutical composition of the present invention may include the form of an anti-cancer adjuvant that enhances the anti-cancer effect of other anti-cancer agents or suppresses or improves the side effects.

In another aspect of the present invention for achieving the above objects, there is provided a method of preventing or treating cancer, comprising administering a pharmaceutically effective amount of the pharmaceutical composition to an individual.

The term “individual” as used herein includes, without limitation, animals such as mammals, including mice, livestock, humans, and the like, that are likely to develop cancer or are affected by cancer.

In the method of preventing or treating cancer of the present invention, the pharmaceutical composition may be administered through any general route, as long as it can reach a target tissue. The pharmaceutical composition of the present invention may be administered, but is not particularly limited to, through various routes such as oral administration, intravenous administration and rectal administration, and in some cases, it may be administered through other routes depending on the purpose.

In another aspect of the present invention for achieving the above objects, there is provided the use of a combination of a CDK4/6 inhibitor and a tricyclic antidepressant; or the use of a composition comprising a CDK4/6 inhibitor and a tricyclic antidepressant as active ingredients, for preventing or treating cancer. In another aspect, there is provided a combination of a CDK4/6 inhibitor and a tricyclic antidepressant; or the use of a composition comprising a CDK4/6 inhibitor and a tricyclic antidepressant, for the preparation of a medicament for treating or preventing cancer.

Advantageous Effects

If the composition comprising a CDK4/6 inhibitor and a tricyclic antidepressant according to the prevention invention is administered in combination, anti-cancer synergistic effects are exhibited such that the survival rate of cancer cells is remarkably reduced compared to that of the group treated with the CDK4/6 inhibitor or tricyclic antidepressant alone. In addition, since it is possible to obtain a high anti-cancer effect while alleviating the side effects of the CDK4/6 inhibitor by administration of the composition according to the present invention, the composition comprising a CDK4/6 inhibitor and a tricyclic antidepressant as active ingredients may be usefully used as a preventive or therapeutic agent for cancer.

DESCRIPTION OF DRAWINGS

FIGS. 3*a* and 3*b* show the results of performing biochemical analysis on blood collected from mice 14 days after desipramine and abemaciclib were administered separately or in combination.

BEST MODE

Figure 1A:
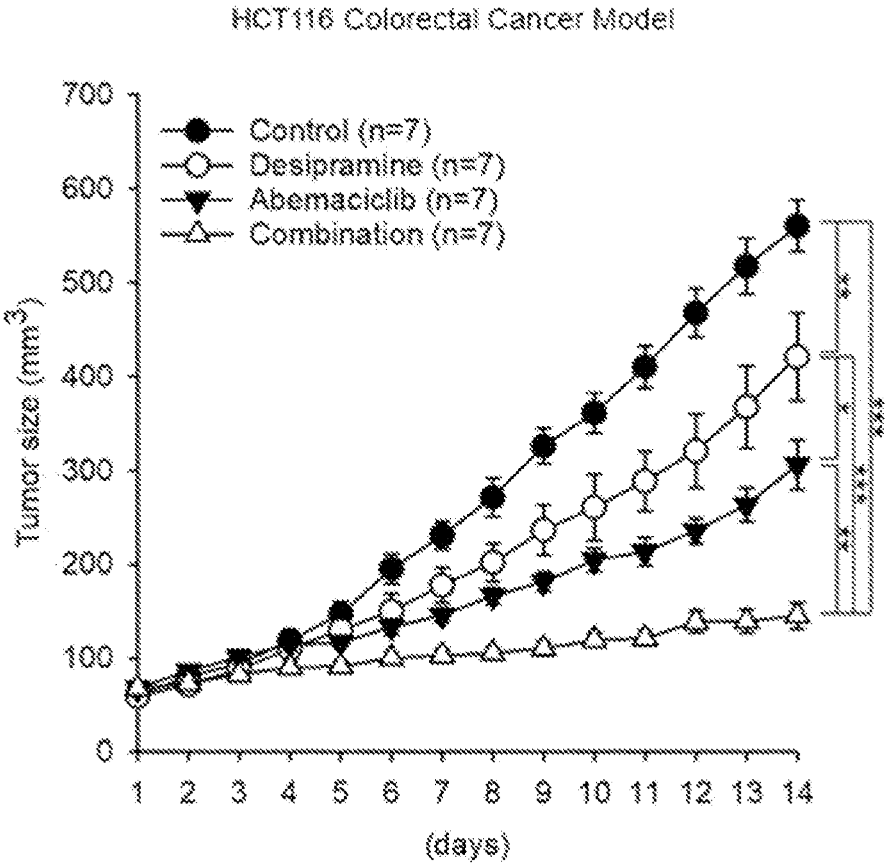
FIG. 1*a* shows the results of measuring the change in tumor size over time when desipramine and abemaciclib were administered separately or in combination.

Hereinafter, the configuration and effects of the present invention will be described in more detail through examples. These examples are only for illustrating the present invention, and the scope of the present invention is not limited thereto.

Example 1: Confirmation of Cancer Cell Killing Effect Following Combined Administration of CDK4/6 Inhibitor and Tricyclic Antidepressant 1.1. Cell Culture This experiment was conducted on the lung cancer cell line H460, the colorectal cancer cell line HCT116, and the breast cancer cell line MCF7. As for the genetic characteristics of each cell line, the lung cancer cell line H460 has a KRAS mutation [p.Q61H], the colorectal cancer cell line HCT116 has a KRAS mutation [p.G13D], and the breast cancer cell line MCF7 has the characteristic of being positive for estrogen receptor and progesterone receptor but negative for HER2. The cell lines H460 and MCF7 were cultured using RPMI1640 medium containing 10% FBS and 1% penicillin-streptomycin, and the cell line HCT116 was cultured using McCoy's 5A medium containing 10% FBS and 1% penicillin-streptomycin.

1.2. Confirmation of Cancer Cell Killing Effect

Cancer cell killing effects were confirmed for various combinations of CDK4/6 inhibitors and tricyclic antidepressants.

Specifically, abemaciclib, ribociclib and palbociclib were used as CDK4/6 inhibitors, and DMSO was used as a solvent to prepare the drug stock. Imipramine, clomipramine, desipramine, amitriptyline and imipramine blue were used as tricyclic antidepressants, distilled water (DW) was used as a solvent to prepare the drug stock, and DMSO was used only for imipramine blue. Each drug was used after diluting to the concentrations shown in Table 1 (antidepressant concentration used (μM)) and Table 2 (CDK4/6 inhibitor concentration used (μM)) below.

The cell lines H460, HCT116 and MCF7 were cultured at $3\times10^3$ cells/well in a 96 well plate. The next day, each drug was prepared at the concentrations shown in Tables 1 and 2, mixed with the medium, and then added to each well and left for 48 hours. After 48 hours, 10 ul/well of WST-1 reagent was added thereto and reacted for 1 hour. Samples reacted with WST-1 were analyzed by ELISA at 450 nM, and the same conditions were repeated three times to calculate the average value and standard error.

TABLE 1

| | Solvent | H460 | HCT116 | MCF7 |
|---|---|---|---|---|
| Imipramine | DW | 100 | 100 | 50 |
| Clomipramine | DW | 40 | 40 | 20 |
| Desipramine | DW | 50 | 20 | 50 |
| Amitriptyline | DW | 45 | 25 | 50 |
| Imipramine blue | DMSO | 0.5 | 0.4 | 0.1 |

TABLE 2

| | Solvent | H460 | HCT116 | MCF7 |
|---|---|---|---|---|
| Abemaciclib | DMSO | 4 | 0.2 | 10 |
| Ribociclib | DMSO | 50 | 20 | 30 |
| Palbociclib | DMSO | 15 | 5 | 20 |

The experimental results for each cell line were observed as follows.

① Anti-Cancer Efficacy Test in Lung Cancer (Cell Line H460)

When treated with 4 μM abemaciclib alone, the lung cancer cell survival rate was found to be 71%, and the survival rates of the antidepressants alone and combined treatment groups were as follows.

TABLE 3

| Cell survival rate (%) | Treatment with antidepressants alone | Combined treatment with abemaciclib |
|---|---|---|
| Imipramine | 78 | 20 |
| Clomipramine | 65 | 20 |
| Desipramine | 40 | 24 |
| Amitriptyline | 65 | 50 |
| Imipramine blue | 62 | 50 |

As shown in Table 3, when the CDK4/6 inhibitor abemaciclib is treated with one of the antidepressants imipramine, clomipramine, desipramine, amitriptyline and imipramine blue, it was confirmed that the cancer cell survival rate was remarkably reduced compared to the group treated with CDK4/6 inhibitors or antidepressants alone, showing an anti-cancer synergy effect.

When treated with 50 μM ribociclib alone, the lung cancer cell survival rate was found to be 72%, and the survival rates of the antidepressants alone and combined treatment groups were as follows.

TABLE 4

| Cell survival rate (%) | Treatment with antidepressant alone | Combined treatment with ribociclib |
|---|---|---|
| Imipramine | 78 | 47 |
| Clomipramine | 65 | 34 |
| Desipramine | 40 | 16 |
| Amitriptyline | 65 | 32 |
| Imipramine blue | 62 | 36 |

As shown in Table 4, when the CDK4/6 inhibitor ribociclib is treated with one of the antidepressants imipramine, clomipramine, desipramine, amitriptyline and imipramine blue, it was confirmed that the cancer cell survival rate was remarkably reduced compared to the group treated with CDK4/6 inhibitors or antidepressants alone, showing an anti-cancer synergy effect.

When treated with 15 μM palbociclib alone, the lung cancer cell survival rate was found to be 67%, and the survival rates of the antidepressants alone and combined treatment groups were as follows.

TABLE 5

| Cell survival rate (%) | Treatment with antidepressant alone | Combined treatment with palbociclib |
|---|---|---|
| Imipramine | 78 | 53 |
| Clomipramine | 65 | 33 |
| Desipramine | 40 | 14 |
| Amitriptyline | 65 | 58 |
| Imipramine blue | 62 | 36 |

As shown in Table 5, when the CDK4/6 inhibitor palbociclib is treated with one of the antidepressants imipramine, clomipramine, desipramine, amitriptyline and imipramine blue, it was confirmed that the cancer cell survival rate was remarkably reduced compared to the group treated with CDK4/6 inhibitors or antidepressants alone, showing an anti-cancer synergy effect.

② Anti-Cancer Efficacy Test in Colorectal Cancer (Cell Line HCT116)

When treated with 0.2 μM abemaciclib alone, the colorectal cancer cell survival rate was found to be 87%, and the survival rates of the antidepressants alone and combined treatment groups were as follows.

TABLE 6

| Cell survival rate (%) | Treatment with antidepressant alone | Combined treatment with abemaciclib |
|---|---|---|
| Imipramine | 77 | 58 |
| Clomipramine | 65 | 32 |
| Desipramine | 71 | 28 |
| Amitriptyline | 86 | 64 |
| Imipramine blue | 53 | 39 |

As shown in Table 6, when the CDK4/6 inhibitor abemaciclib is treated with one of the antidepressants imipramine, clomipramine, desipramine, amitriptyline and imipramine blue, it was confirmed that the cancer cell survival rate was remarkably reduced compared to the group treated with CDK4/6 inhibitors or antidepressants alone, showing an anti-cancer synergy effect.

When treated with 20 μM ribociclib alone, the colorectal cancer cell survival rate was found to be 73%, and the survival rates of the antidepressants alone and combined treatment groups were as follows.

TABLE 7

| Cell survival rate (%) | Treatment with antidepressants alone | Combined treatment with ribociclib |
|---|---|---|
| Imipramine | 77 | 39 |
| Clomipramine | 65 | 23 |
| Desipramine | 71 | 29 |
| Amitriptyline | 86 | 46 |
| Imipramine blue | 53 | 31 |

As shown in Table 7, when the CDK4/6 inhibitor ribociclib is treated with one of the antidepressants imipramine, clomipramine, desipramine, amitriptyline and imipramine blue, it was confirmed that the cancer cell survival rate was remarkably reduced compared to the group treated with CDK4/6 inhibitors or antidepressants alone, showing an anti-cancer synergy effect.

When treated with 5 μM palbociclib alone, the lung cancer cell survival rate was found to be 79%, and the survival rates of the antidepressants alone and combined treatment groups were as follows.

TABLE 8

| Cell survival rate (%) | Treatment with antidepressants alone | Combined treatment with palbociclib |
|---|---|---|
| Imipramine | 77 | 41 |
| Clomipramine | 65 | 34 |
| Desipramine | 71 | 44 |
| Amitriptyline | 86 | 54 |
| Imipramine blue | 53 | 43 |

As shown in Table 8, when the CDK4/6 inhibitor palbociclib is treated with one of the antidepressants imipramine, clomipramine, desipramine, amitriptyline and imipramine blue, it was confirmed that the cancer cell survival rate was remarkably reduced compared to the group treated with CDK4/6 inhibitors or antidepressants alone, showing an anti-cancer synergy effect.

③ Anti-Cancer Efficacy Test in Breast Cancer (Cell Line MCF7)

When treated with 10 μM abemaciclib alone, the breast cancer cell survival rate was found to be 59%, and the survival rates of the antidepressants alone and combined treatment groups were as follows.

TABLE 9

| Cell survival rate (%) | Treatment with antidepressants alone | Combined treatment with abemaciclib |
|---|---|---|
| Imipramine | 83 | 34 |
| Clomipramine | 81 | 37 |
| Desipramine | 60 | 21 |
| Amitriptyline | 63 | 21 |
| Imipramine blue | 88 | 43 |

As shown in Table 9, when the CDK4/6 inhibitor abemaciclib is treated with one of the antidepressants imipramine, clomipramine, desipramine, amitriptyline and imipramine blue, it was confirmed that the cancer cell survival rate was remarkably reduced compared to the group treated with CDK4/6 inhibitors or antidepressants alone, showing an anti-cancer synergy effect.

When treated with 30 μM ribociclib alone, the breast cancer cell survival rate was found to be 80%, and the survival rates of the antidepressants alone and combined treatment groups were as follows.

TABLE 10

| Cell survival rate (%) | Treatment with antidepressants alone | Combined treatment with ribociclib |
|---|---|---|
| Imipramine | 83 | 55 |
| Clomipramine | 81 | 56 |
| Desipramine | 60 | 28 |
| Amitriptyline | 63 | 28 |
| Imipramine blue | 88 | 60 |

As shown in Table 10, when the CDK4/6 inhibitor ribociclib is treated with one of the antidepressants imipramine, clomipramine, desipramine, amitriptyline and imipramine blue, it was confirmed that the cancer cell survival rate was remarkably reduced compared to the group treated with CDK4/6 inhibitors or antidepressants alone, showing an anti-cancer synergy effect.

When treated with 20 μM palbociclib alone, the breast cancer cell survival rate was found to be 75%, and the survival rates of the antidepressants alone and combined treatment groups were as follows.

TABLE 11

| Cell survival rate (%) | Treatment with antidepressants alone | Combined treatment with palbociclib |
|---|---|---|
| Imipramine | 83 | 53 |
| Clomipramine | 81 | 43 |
| Desipramine | 60 | 45 |
| Amitriptyline | 63 | 45 |
| Imipramine blue | 88 | 59 |

As shown in Table 11, when the CDK4/6 inhibitor palbociclib is treated with one of the antidepressants imipramine, clomipramine, desipramine, amitriptyline and amitriptyline, it was confirmed that the cancer cell survival rate was remarkably reduced compared to the group treated with CDK4/6 inhibitors or antidepressants alone, showing an anti-cancer synergy effect.

Example 2: Analysis of Tumor Growth Inhibitory Effect Following Combined Administration of Desipramine and Abemaciclib

2.1. Construction of Tumor Model

In order to evaluate the improvement of therapeutic effect following the combined treatment of desipramine and abemaciclib, a subcutaneous tumor model was constructed using the colorectal cancer cell line HCT116.

Specifically, the human colorectal cancer cell line HCT116 was purchased from the American Type Culture Collection (ATCC, USA) and cultured in McCoy's 5A medium containing 10% fetal bovine serum (FBS) and penicillin-streptomycin under conditions of 37° C., 5% carbon dioxide and standard humidity. HCT116 cancer cells were injected subcutaneously into nude mice (Balb/c nude) at an amount of $5\times10^6$ cells/100 μL, and tumors were confirmed to be formed about 7-10 days later. When the tumor size reached 60-70 $mm^3$, the mice were divided into 4 groups (negative control group, desipramine alone treatment group, abemaciclib alone treatment group, and desipramine and abemaciclib combined treatment group), and the experiment was conducted. Desipramine was injected intraperitoneally at a dose of 20 mg/kg, and abemaciclib was administered orally at a dose of 30 mg/kg. Desipramine and abemaciclib were administered once a day until the end of the experiment, and vehicle was administered to the control group.

2.2. Analysis of Tumor Growth Inhibitory Effect

Figure 1B:
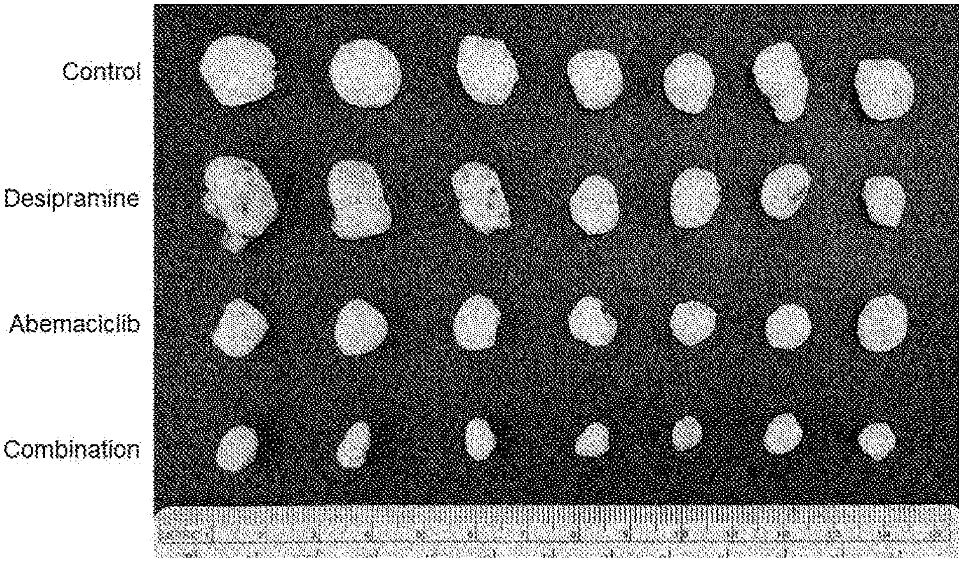
FIG. 1*b* shows the results of comparing tumor sizes in the alone and combined administration groups 14 days after desipramine and abemaciclib were administered separately or in combination.

To evaluate the anti-tumor effect, the tumor size was measured every day until day 14 after treatment, and the differences between each group were analyzed. The tumor size was calculated as follows: V ($mm^3$)=1/2×long axis (mm)×short axis (mm)×height (mm). By day 14, the tumor size was measured, a tumor growth graph was created, and the tumor size between each group was compared and analyzed. As can be seen in the results of FIGS. 1*a* and 1*b*, it could be confirmed that the anti-tumor effect was the best in the desipramine and abemaciclib combined treatment group, and on day 14, it was confirmed that the tumor sizes in the desipramine alone treatment group, abemaciclib alone treatment group, and desipramine and abemaciclib combined treatment group were measured to be 75.2% ($P<0.01$), 54.6% (*$P<0.001$) and 25.9% (*$P<0.001$), respectively, and there was an anti-cancer synergistic effect in the combined treatment group compared to the alone treatment group (FIG. 1**).

Example 3: Toxicity Evaluation by Drug Administration

In order to evaluate the biotoxic effect of the administration of desipramine and abemaciclib, major normal organs such as heart, lung, liver, spleen and kidney were collected on day 14, and sections were prepared, and then histological changes were confirmed through hematoxylin and eosin staining.

Figure 2A:
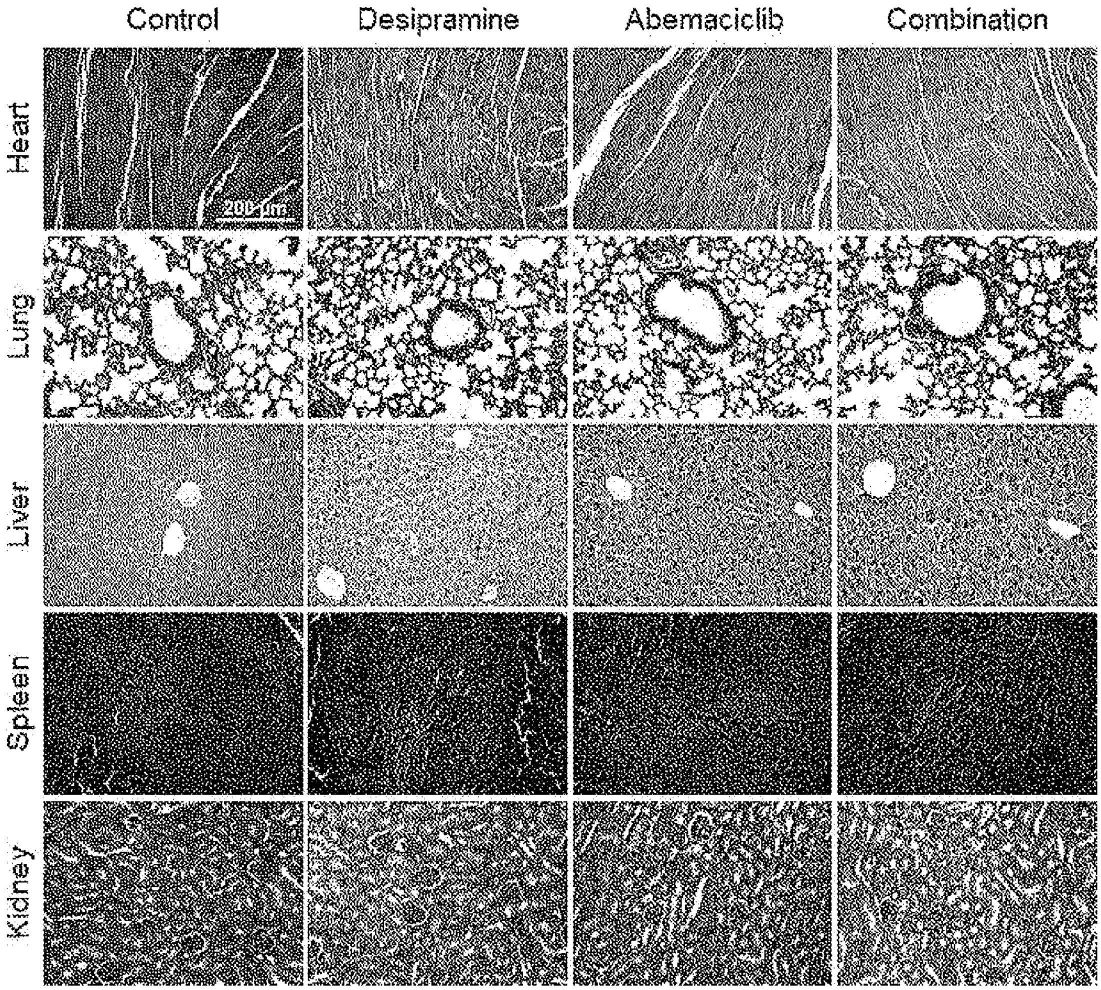
FIG. 2*a* shows the results of hematoxylin and eosin staining of the heart, lung, liver, spleen and kidney in the alone and combined administration groups 14 days after desipramine and abemaciclib were administered separately or in combination.
Figure 2B:
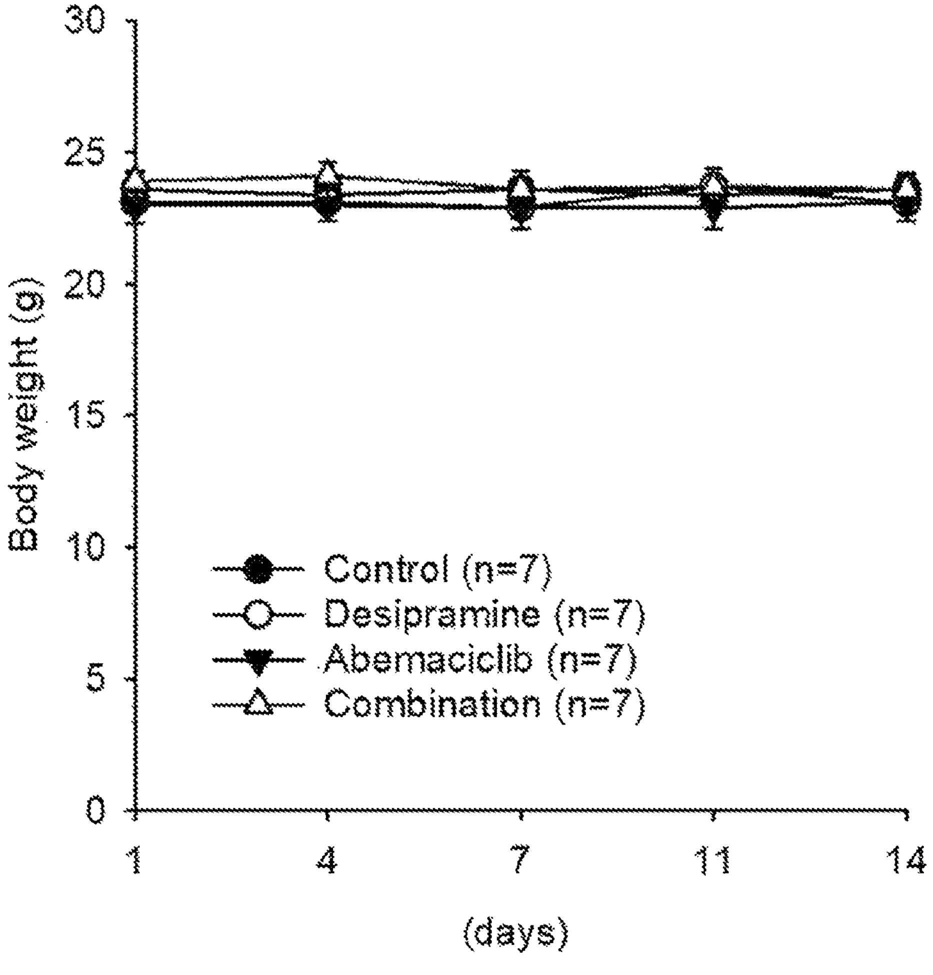
FIG. 2*b* shows the results of measuring the change in body weight of mice over time in the desipramine and abemaciclib alone and combined administration groups.

As a result of biopsy of major organs for the groups administered desipramine and abemaciclib separately or in combination, no histological changes were observed compared to the control group (FIG. 2*a*). In addition, as a result of measuring body weight for 14 days for the groups administered desipramine and abemaciclib separately or in combination, no significant difference in body weight was observed between each group (FIG. 2*b*).

Figure 3A:
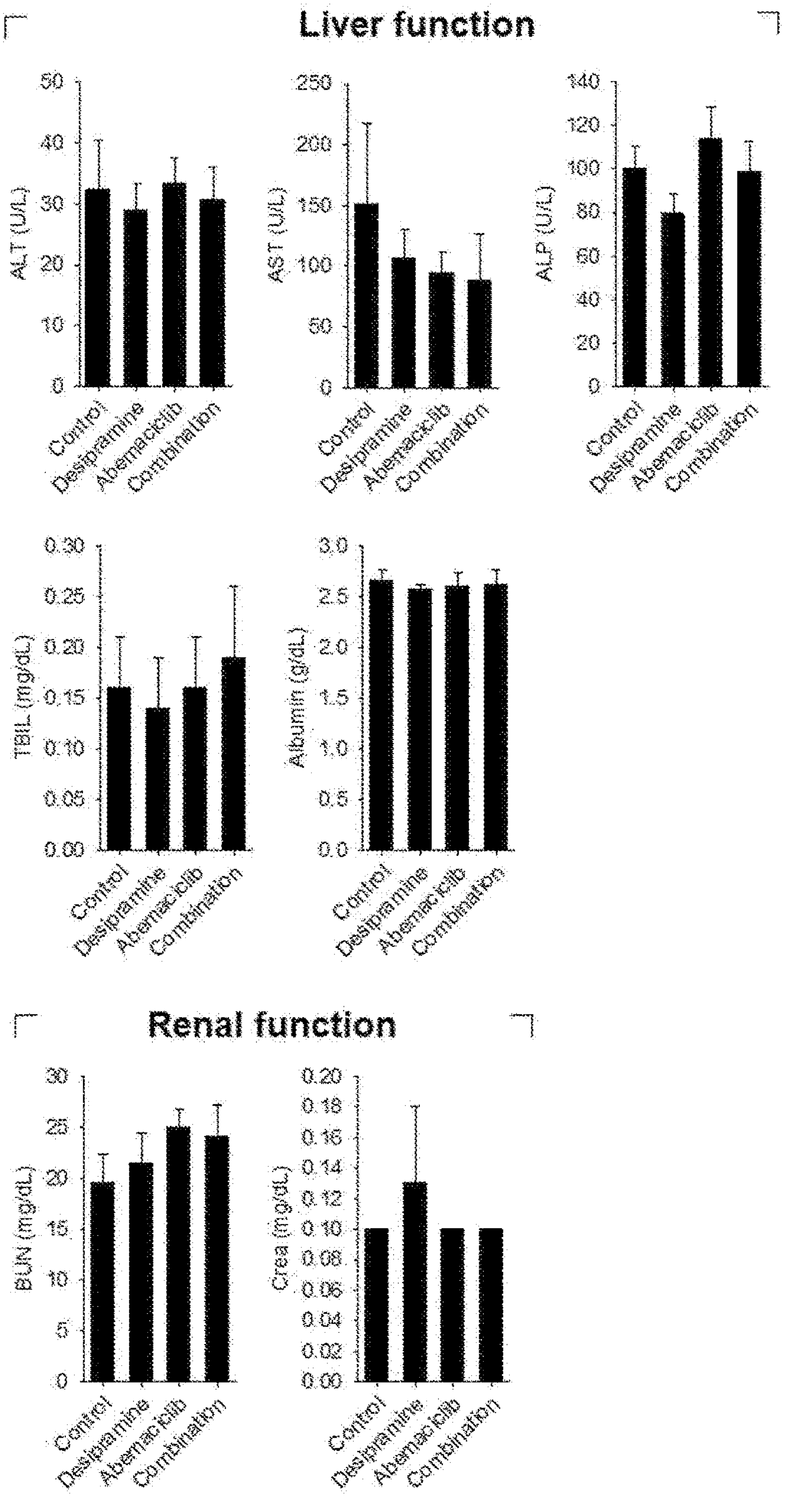

When blood was collected from mice and blood biochemical analysis was performed on day 14 after treatment for the groups administered desipramine and abemaciclib separately or in combination, no significant differences in various toxicity-related factors in the blood were found between each group (FIG. 3). Considering these results together, it was confirmed that the combined dose of desipramine and abemaciclib resulted in a synergistic cancer therapeutic effect and did not cause toxicity to normal tissues.

What is claimed is:

1. A pharmaceutical composition for treating cancer, comprising a CDK4/6 inhibitor and a tricyclic antidepressant as active ingredients, wherein the cancer is lung cancer, colorectal cancer, or breast cancer, and the CDK4/6 inhibitor is abemaciclib, ribociclib, or palbociclib.

2. The pharmaceutical composition according to claim 1, wherein the tricyclic antidepressant is 7-OH-amoxapine, amezepine, amineptine, amitriptyline, amitriptylinexide, amoxapine, aptazapine, azepindole, azipramine, batelapine, butriptyline, cianopramine, ciclazindol, ciclopramine, cidoxepin, clomipramine, cotriptyline, cyanodothiepin, demexiptiline, depramine (balipramine), desipramine (desmethylimipramine), desmethylclomipramine, desmethyltrimipramine, dibenzepin, dimetacrine, dosulepin (dothiepin), doxepin, enprazepine, esmirtazapine, fantridone, fluotracen, hepzidine, homopipramol, imipramine, imipraminoxide, intriptyline, iprindole, ketipramine, litracen, lofepramine, losindole, loxapine, maprotiline, mariptiline, mazindol, melitracen, metapramine, mezepine, mianserin, mirtazapine, monometarine, naranol, nitroxazepine, norbutriptyline, nordoxepin, northiaden (nordosulepin), nortriptyline (noramitriptyline), noxiptiline, octriptyline, opipramol, oxaprotiline, pipofezine, pirandamine, promethazine, propizepine, protriptyline, quinupramine, setiptiline (teciptiline), spiroxepin, tandamine, tampramine, tianeptine, tienopramine, trimipramine, or imipramine blue.

3. The pharmaceutical composition according to claim 1, wherein the pharmaceutical composition is for combined administration of the CDK4/6 inhibitor and the tricyclic antidepressant.

4. The pharmaceutical composition according to claim 3, wherein the pharmaceutical composition is in the form of a mixture in which the CDK4/6 inhibitor and the tricyclic antidepressant are mixed, or the CDK4/6 inhibitor and the tricyclic antidepressant are separately formulated and administered simultaneously or sequentially.

5. The pharmaceutical composition according to claim 1, wherein the pharmaceutical composition further comprises a pharmaceutically acceptable carrier, excipient, or diluent.

6. The pharmaceutical composition according to claim 3, wherein the pharmaceutical composition is in the form of a mixture in which the CDK4/6 inhibitor and the tricyclic antidepressant are mixed.

7. The pharmaceutical composition according to claim 3, wherein the CDK4/6 inhibitor and the tricyclic antidepressant are separately formulated and administered simultaneously.

8. The pharmaceutical composition according to claim 3, wherein the CDK4/6 inhibitor and the tricyclic antidepressant are separately formulated and administered sequentially.

* * * * *